United States Patent [19]

Six et al.

[11] Patent Number: 5,464,630

[45] Date of Patent: Nov. 7, 1995

[54] LIPOSOMES THAT PROVIDE THYMIC DEPENDENT HELP TO WEAK VACCINE ANTIGENS

[75] Inventors: Howard R. Six, East Stroudburg, Pa.; Nathalie B. Garcon, Rixensart, Belgium

[73] Assignee: Research Development Foundation, Carson City, Nev.

[21] Appl. No.: 380,213

[22] Filed: Jan. 30, 1995

Related U.S. Application Data

[63] Continuation of Ser. No. 94,398, Jul. 19, 1993, abandoned, which is a continuation of Ser. No. 821,242, Jan. 10, 1992, abandoned, which is a continuation of Ser. No. 558,960, Jul. 27, 1990, abandoned.

[51] Int. Cl.$^6$ ............................................. A61K 9/127
[52] U.S. Cl. ............................................ 424/450; 436/829
[58] Field of Search ........................ 424/450, 204.1, 424/206.1, 210.1; 436/829

[56] References Cited

U.S. PATENT DOCUMENTS

| | | | |
|---|---|---|---|
| 3,752,886 | 8/1973 | Munder et al. | 424/199 |
| 4,053,585 | 10/1977 | Allison et al. | 424/92 |
| 4,196,191 | 4/1980 | Almeida et al. | 424/89 |
| 4,199,565 | 4/1980 | Fullerton | 424/89 |
| 4,235,871 | 11/1980 | Papahadjopoulos | 424/264 |
| 4,396,630 | 8/1983 | Riedl et al. | 424/365 |
| 4,448,765 | 5/1984 | Ash et al. | 424/14 |
| 4,565,696 | 1/1986 | Heath | 424/88 |
| 4,673,574 | 6/1987 | Anderson | 424/94 |
| 4,708,933 | 11/1987 | Huang et al. | 435/7 |
| 4,761,283 | 8/1988 | Anderson | 424/92 |
| 4,797,285 | 1/1989 | Barenbolz et al. | 424/450 |
| 4,882,145 | 11/1989 | Thornton | 424/88 |
| 4,902,506 | 2/1990 | Anderson et al. | 424/92 |

FOREIGN PATENT DOCUMENTS 0191536   8/1986   European Pat. Off. .

OTHER PUBLICATIONS

J. Exp. Med., 1986, Scherle, P. A. and W. Gerhard, 164:1114–1128.

Annals New York Academy of Sciences, 1978, Kinsky, S. C., pp. 111–120.

Elsevier Science Publishers B.V., 1988, Bogdanov, A A et al. 231(2): 381–384.

Am. Asso. Immunologists, Apr. 1988, Garcon, N. and H. R. Six (Abstract).

Kochibe et al., "Stimulation and inhibition of anti–hapten responses in guinea pigs immunized with hybrid liposomes", Proc. Nat. Acad. Sci. USA, vol. 72, No. 11, pp. 4582–4586, Nov. 1975.

*Primary Examiner*—Gollamudi S. Kishore
*Attorney, Agent, or Firm*—Benjamin Aaron Adler

[57] ABSTRACT

The antibody response to a target antigen may be enhanced by incorporating the antigen into a liposome along with an additional constituent which contains at least one T-helper lymphocyte recognition site. The liposomes can include a wide variety of lipid materials. Both the antigen and the T-helper lymphocite recognition site containing constituent may be associated with the liposome by using hydrophobic interactions or by covalent attachment to a lipid.

12 Claims, No Drawings

LIPOSOMES THAT PROVIDE THYMIC DEPENDENT HELP TO WEAK VACCINE ANTIGENS

This is a continuation of application Ser. No. 08/094,398 filed on Jul. 19, 1993, now abandoned, which is a continuation of application Ser. No. 07/821,242 filed on Jan. 10, 1992, now abandoned, which is a continuation of application Ser. No. 07/558,960 filed on Jul. 27, 1990, now abandoned.

BACKGROUND OF THE INVENTION

1. Field of the Invention

The invention relates to enhancing the antibody response to a target antigen, by incorporating the antigen into a liposome along with an additional constituent which contains at least one T-helper lymphocyte recognition site.

2. Description of the Related Technology

A vaccine antigen confers immunity to infection by inducing the organism to produce an immune response. Antigens are, therefore, of varying usefulness depending on the strength of the immune response they induce. There are to varying degrees inherently strong and weak antigens. Additionally, antigens can be classified as thymic ("T") dependent or T-independent antigens based on whether they are capable of eliciting helper activity from T-cells. This T-cell activity is associated with the production of antibodies of the IgG and IgA classes. T-independent antigens induce the production of IgM antibodies, but do not induce the B-cells to switch to the synthesis of IgG or IgA antibodies. The production of immunoglobulins of the IgM class is a transient response in laboratory animals and humans, lasting only a few months; whereas the production of antibodies of the IgG and IgA classes usually persist for years. It is, therefore, beneficial to elicit a T-dependent response to a particular antigen. Carbohydrate or polysaccharide based antigens are T-independent antigens and are of limited usefulness as vaccines in children. Similarly, many polypeptides which represent antibody recognition sites are T-independent antigens and are, therefore, likewise incapable of generating the IgG and IgA antibody responses that are desired for a vaccine.

It is known that a stronger antibody response can be elicited to a weak antigen by conjugating (covalently attaching) the antigen to a helper protein which enhances the immune response. For example, in U.S. Pat. No. 4,761,283 it was shown that the weak immunogenic response to certain bacterial capsular polymers was enhanced by conjugating the antigen to a bacterial helper protein which, in itself, induces an antigenic response. It is common to use a toxin as the helper protein, such as for example, Diphtheria Toxoid. Use of such a toxic helper protein creates a problem, however because the intrinsic toxicity of the helper protein may limit the dosage of the antigen-helper protein conjugate and therefore limit its effectiveness.

It is also common that the immune response to the target antigen is suppressed due to a previous immunization of the organism to the helper protein creating an epitope suppression effect. When the host organism is primed to react to the helper protein, the organism will clear the body of the target antigen-helper protein conjugate before the organism can initiate an immunological response to the target antigen.

These previously used conjugates are formed by covalently linking the antigen to the carrier helper protein. The immune response enhancement is of particular importance for T-independent antigens which can be conjugated to a peptide containing at least one T-helper cell recognition site, thereby obtaining a T-dependent response to a T-independent antigen. The presently used covalently linked conjugates are, however, limited in their effectiveness because of the structural limitations imposed by the covalent binding process, i.e., conformational changes, potential inaccessibility of binding sites, and inability to vary the ratios of the components. In addition, these conjugates may exhibit dose limitations and an epitope suppression effect.

Liposomes are membranous vesicles formed by the dispersion of lipids in aqueous media. Methods for the preparation of liposomes are well known to those skilled in the art, and are exemplified but not limited to any of the following patents which are incorporated herein by reference: U.S. Pat. Nos. 4,565,696 and 4,235,871. Liposomes possess several properties required for an in-vivo carrier; low toxicity, low immunogenicity, and biodegradability. It has also been shown that liposomes can enhance the antibody response to antigens in laboratory animals. The antigens are either entrapped within the aqueous compartments of the liposome or associated with the bilayer. For example, U.S. Pat. No. 4,565,696 describes a process for linking immunogens covalently to the surface bilayer of the liposome and thereby potentiating the immune response.

SUMMARY OF THE INVENTION

The present invention relates to providing an enhanced antigenic response to a target antigen by incorporating the antigen into a liposome preparation along with at least one helper peptide, such helper peptide containing at least one T-cell recognition site. The present invention can be used to elicit an enhanced antigenic response to any antigen; including but not limited to polysaccharides such as Hemophilus influenzae, Meningococci, Pneumococci and Streptococci and peptides such as hepatitis B surface proteins, HIV surface proteins, influenza virus proteins, parainfluenza virus peptides or hemagglutinin, respiratory syncytial virus surface glycoproteins, and cholera surface glycoproteins.

The target antigen (to which the enhanced immunogenic response is desired) can be incorporated into the liposomal vesicle by attaching the antigen to one of a wide variety of lipid materials containing an active functionality. These lipid materials include phosphatidyl ethers or phosphatidyl esters (e.g., phosphatidylethanolamine and phosphatidylcholine), glycerides, cerebrosides, gangliosides, sphingomyelins, and steroids (e.g., cholesterol) etc. U.S. Pat. No. 4,565,696, and U.S. Pat. No. 4,235,871 disclose additional lipid materials for use in the preparation of liposomes.

Alternatively, the target antigen may be incorporated into the liposomal vesicle via hydrophobic forces if the antigen carries a lipophilic group, see U.S. Pat. No. 4,448,765, or a hydrophobic group can be attached to the antigen.

Incorporation of the helper peptide may also occur using either covalent or hydrophobic interactions. For example, the hemagglutinin (HA) protein of influenza virus is composed of two polypeptide cahains ($HA_1$ and $HA_2$). The $HA_2$ polypeptide chain contains a sequence of hydrophobic amino acids located near the carboxy-terminus of the polypeptide and contains at least one T-helper cell recognition site. Thus, the $HA_2$ polypeptide chain can be incorporated into liposomes via the transmembrane hydrophobic region. U.S. Pat. No. 4,448,765 describes the incorporation of influenza virus subunits into liposomes and is incorporated herein by reference. The hydrophobic component can alternatively be added to the helper peptide in order to facilitate association with the liposomal membrane, or the helper peptide can be covalently attached directly to lipid materials containing an active functionality.

The present invention has several advantages over the previously used antigen-carrier conjugates as, for example, is disclosed in U.S. Pat. No. 4,761,283. In the covalently bonded conjugates, alterations in the carrier protein conformation as well as alterations in the antigen conformation are possible due to the covalent bond. This disadvantage may be overcome in the present invention wherein the target antigen and the helper peptide are associated with a liposome. The present invention overcomes the toxicity and epitope suppression effects associated with the prior art. The present invention uses non-toxic lipids, and is preferably used with isolated, non-toxic T-helper site containing peptides.

The present invention is also advantageous over previously used conjugates because it allows for modifications in the antigen density, the ratio of target antigen to helper peptide, and for incorporation of more than one T-helper cell recognition site bearing helper peptide. These factors can influence the quantities of specific antibodies produced to the target antigen. These factors are not easily controlled when conjugates are synthesized because the two components must be covalently bound, creating physical limitations as to the number and type of factors which can be associated together while retaining access to the recognition sites. Additionally, the present invention is advantageous over the conjugates because incorporation of an antigen into a liposome has been shown to enhance antibody production. Thus, the present invention uses this property of liposomes to additionally enhance the production of antibodies to a given antigen, and particularly to weak antigens which would not cause sufficient antibody production.

The liposomal vesicles of this invention provide a new approach to the design of synthetic vaccines. Multiple copies of the target antigen and the helper peptide or peptides can be incorporated in a fast and easy method. In addition to providing effective and enhanced immunization to the target antigen, the approach allows for easy testing of antigens and helper peptides. For example, the present invention provides a simple vehicle for comparison of the ability of various T-helper peptides to enhance the immunogenic response to a given antigen. Thus, the present invention also provides a useful vehicle for probing the mechanism of the immune response.

Other and further embodiments, features and advantages will be apparent from the following description of the presently preferred embodiment of the invention.

DETAILED DESCRIPTION OF THE PREFERRED EMBODIMENT

The vaccine composition of the present invention may be utilized to enhance the immune response to any target antigen and most preferably to T-independent antigens. The present invention is exemplified with reference to DNP-CapPE which has been well studied as a T-independent antigen. It would, however, be obvious to one skilled in the art that the present invention is applicable to any antigen. In the preferred embodiment of the present invention, a synthetic vaccine is synthesized which induces a T-dependent immunological response to a T-independent antigen. The target antigen is incorporated into a liposomal preparation along with a helper peptide or peptides which contain a T-cell recognition site. Any peptide which contains a T-cell recognition site may be used as the helper peptide, for example native or detoxified peptides from toxoids such as influenza, tetanus, diptheria pseudomonas, staphylococcus, streptococcus, pertussis and Escherichia Coli. A simple test can be performed to determine if a candidate peptide contains a T-cell recognition site. The peptide is incorporated into a liposomal preparation along with an antigen such as DNP-CapPE, which contains only a B-cell epitope. If there is an IgG response to the resulting liposomal preparation in a host organism, then the peptide has a T-cell recognition site and can serve as the helper peptide of the present invention.

The $HA_2$ subunit of the influenza hemagglutinin protein was preferably used as the helper peptide because it has been well defined and is known to possess at least one T-helper cell recognition site but no B-cell recognition site. Thus, this peptide causes a T-dependent immunological response to a conjugated antigen but does not induce an antibody response against itself. This limitation is not required for the functioning of the invention; any helper peptide may also be utilized which contains a B-cell recognition site if an immunological response to the helper peptide is desired or is acceptable in addition to a response to the target antigen. It is, however, preferred that the helper peptide be a pure T-helper cell epitope. Similary, any helper peptide may also be utilized which contains a T-cytotoxic lymphocyte recognition site if a cytotoxic response is desired or is acceptable in addition to a response to the target antigen.

The $HA_2$ subunit is further appropriate as a helper peptide because it carries a hydrophobic sequence of amino acids near the carboxy terminus that normally extends through the lipid envelope of the virus. This transmembrane region facilitates association with the lipid bilayers of liposomes and $HA_2$ is quantitatively associated with the liposomal vesicles. As discussed previously, alternative methods of incorporating the helper peptide are also possible, such as, for example, covalently attaching the peptide to a lipid, or attaching a hydrophobic sequence of amino acids to one end of the peptide. It would be obvious to one skilled in the art that various methods for incorporating the helper peptide into the liposome are possible.

DNP-CapPE was chosen as a target antigen because it has been well studied and is a T-independent antigen. Thus, in the following experiments a T-dependent response to DNP-CapPE arises from the influence of the helper peptide. The liposomal preparation of the present invention can be used to augment the immune response in an individual. The term "individual" is meant to include any animal, preferably a mammal, and most preferably a dog, cat, cow, horse or human.

Example 1

Preparation of liposomes.

A wide variety of lipid materials may be used to practice the present invention, including but not limited to phosphatidyl ethers or phosphatidyl esters (e.g., phosphatidylethanolamine and phosphatidylcholine), glycerides, cerebrosides, gangliosides, sphingomyelins, and steroids (e.g., cholesterol). The following is an example of a preparation using phosphatidylcholine, although one skilled in the art would recognize that any liposomal preparation technique could be used which allows for the incorporation of the target antigen and the helper protein or proteins. Prior to preparation of the liposome, it may be necessary to covalently attach the target antigen and/or the helper peptide to one of the lipid components according to one of the well known methods in order to facilitate incorporation. Phosphatidylcholine (PC)

(Avanti polar lipids, Pelham, Ala.) purified from egg yolk (EYPC) was used to prepare the liposomes. EYPC was added to a round bottom flask in the desired quantity and chloroform was removed in a rotating evaporator (Buchi 461). The dried lipid film was resuspended in sterile water or phosphate buffered saline (PBS) in quantities sufficient to produce a 10 mM solution of EYPC. When the DNP-CapPE antigen was incorporated into the liposomes, N-2(2, 4 dinitrophenyl E-aminocaproylphosphatidylethanolamine (DNP-CapPE) was added to the chloroform solution of EYPC. Purified $HA_2$ subunit (provided by Doris Bucher, Mt. Sinia, N.Y.) derived from the hemagglutinin (HA) of A/USSR-90/77 $H_1N_1$ virus was also added to the lipid film for inclusion in liposomes. Liposomes were then formed either by suspension of the lipid mixture in sterile PBS or by dissolving the lipid mixture in n-octylglucoside (5% w/vol in PBS) followed by dialysis against PBS for 16 hours. The quantities of DNP-CapPE and $HA_2$ included in individual liposome preparations were varied to meet the needs of the experiment.

Example 2

Liposome characterization:

In order to assay the association of $HA_2$ to the liposome structures $I^{125}HA_2$ was used To assay the incorporation of DNP-CapPE to the liposomes, aliquots (10 ul) of the initial suspension was dissolved in 990 ul methanol and absorbance at a wavelength of 360 mM was read on a spectrophotometer. The percentage association of $HA_2$ in the preparations, following reconstitution with PBS and dialysis, did not change significantly with varying amounts of $HA_2$, being over 90%. The percentage association of DNP-CapPE in the preparation was greater than 95% in all preparations. No release of the DNP was observed between injections. The DNP-CapPE stayed associated with the liposomal structures.

Example 3

Immunization protocol.

Female outbred albino IRC mice (Timco, Houston, Tex.) were used at 6 to 8 weeks of age. The animals were bled from the tail vein and then given 0.1 ml of placebo (PBS), control liposomes (no $HA_2$ or hapten) or liposomes containing the indicated quantities of hapten and/or $HA_2$ peptide. Three to four weeks later the mice were bled from the tail vein and given a booster inoculation with the same preparation and the same quantity as the initial inoculation. Nine to 14 days later the animals were again bled from the tail vein. Optionally, the mice were given a third inoculation eight weeks after the last injection and they were bled two weeks later. All inoculations were given intramuscularly (IM) in the rear legs. The mice were maintained in plastic cages (4 animals per cage) with barrier filters and they were allowed food and water at libitum. Serum was separated by centrifugation at 2000×g for 5 mn at 4° C. and stored at −20° C until tested. All the serum specimens from each experiment were assayed for antibody production in a single test.

Example 4

Anti-dinitrophenyl (DNP) serum antibody tests.

Dinitrophenylated bovine serum albumin (DNP-BSA) was used to test the antigen, underivatized BSA was used as a control antigen. DNP-BSA was prepared by addition of dinitrofluorobenzene to a solution of BSA at a molar ratio of 10:1; triethanolamine was added until a pH of 9 to 9.5 was reached. After incubation at 20° C. for 16 hours, unbound DNP was removed by dialysis against PBS. Preliminary experiments established that BSA derivatized at this molar ratio detected serum antibody more efficiently than protein containing higher or lower molar ratios of DNP. Serum antibody levels were determined by both ELISA and SPIRA procedures.

ELISA: Immulon I plates (Dynatech, Detroit, Mich.) were coated with DNP-BSA (10 ug per well) in 0.05M carbonate buffer (pH 9.6), control wells were coated with 10 ug per well of BSA. After 16 hours at 4° C., the plates were postcoated with 5% (Vol/Vol) of FCS in PBS. After this and every other incubation, the plates were washed with PBS containing 1% FCS and 0.2% Tween 20. Serial two-fold dilutions of serum starting at 1:100 were prepared in PBS containing 1% BSA in duplicate and 0.1 ml samples of each dilution were added to antigen and control wells. After incubation for 5 hours at 20° C., goat antibodies specific for murine IgG heavy chain alkaline phosphatase conjugated, (Fc specific, Cappel lab, West Chester, Pa.), or goat anti murine IgG subclasses were added at a concentration determined in preliminary experiments to be in excess of that needed for optimal detection of antibody. In the case of IgG subclasses, alkaline phosphatase conjugated swine antibodies specific for goat IgG were then added. P-nitrophenyl phosphate (lmg/ml) in 10% diethanolamine buffer at pH 9.8 was added (0.1 ml per well). Optical densities at 410 nm were read ½ hour later in a Dynatech MR 600 spectrophotometer. Antibody titers are expressed as the highest dilution serum that yielded an optical density of 0.2 above the control wells.

SPIRA: Assessments of DNP antibody levels by SPIRA were determined as described for the ELISA assay with two modifications. Flexible polyvinylchloride microtiter plates were used and $^{125}I$-labeled affinity purified (heavy chain specific) rabbit anti-mouse IgG was used to detect murine antibody bound to the DNP antigen. Antibody titers were calculated as described previously and specificity of the labeled rabbit anti-murine antibodies was established by standard cross-hatch tests using murine-monoclonal antibodies with specificity for the $HA_2$ of influenza virus as described.

Comparisons of antibody titers were made according to the Mann-Witney test when two groups of mice were included in a single experiment. When comparisons between more than two groups were involved, the method of Krusdall-Wallis was used.

Example 5

Immunogenicity of liposomes containing DNP-CapPE and/or HA2 subunit.

Groups of outbred mice were injected twice 4 weeks apart, with preparations of EYPC liposomes (750 ug), or EYPC liposomes containing $HA_2$ (3.7 ug), DNP-CapPE (30 ug) or both (Table 1). IgG and IgM responses were analyzed by indirect ELISA and are expressed as the mean of antibody titers. The lipid to DNP and $HA_2$ molar ratio was 6000:200:1. ELISA readings showed that both preparations containing DNP-CapPE (with or without $HA_2$) generated an IgM response in 7 of 7 mice. However, when titering anti DNP IgG serum antibodies, results were drastically reduced in the liposome DNP group, given titers similar to the control groups, while mice immunized with DNP/$HA_2$ liposomes induced significantly higher levels of serum specific anti DNP IgG.

TABLE 1

| Liposome Composition | IgG Titer | Respondent Ratio | IgM Titer | Respondent Ratio |
|---|---|---|---|---|
| PBS | 210 ± 55 | 3/7 | 119 ± 21 | 3/7 |
| Liposome empty | 313 ± 145 | 3/7 | 290 ± 85 | 3/7 |
| HA$_2$ | 205 ± 65 | 3/7 | 384 ± 190 | 3/7 |
| DNP | 188 ± 73 | 3/7 | 1312 ± 791 | 7/7 |
| DNA-CapPE/HA$_2$ | 1974 ± 925 | 7/7 | 1490 ± 506 | 7/7 |

This shift in immunoglobulin classes is attributable solely to the association of HA$_2$ and DNP within the same liposome structures since no IgG anti DNP antibodies were generated when immunizing the mice with either a mixture of HA$_2$ and DNP-CapPE in aqueous solution or DNP-CapPE liposomes and HA$_2$ liposomes injected together (Table 2). Both components are necessary together in the same liposome in order to stimulate the production of IgG anti DNP antibodies.

When IgG ELISA values (Table 2) were analyzed statistically, responses for a given amount of HA$_2$ (1, 3 or 9 ug) and increasing amount of DNP-CapPE (5, 10 or 30 ug) showed significant differences establishing a dose response effect for both DNP and HA$_2$. This again shows that the enhanced IgG production is due to the presence of both the target antigen and the helper peptide in the same liposome. Mice immunized with DNP-BSA gave an IgG response comparable to the group immunized with the highest does of HA$_2$ and DNP in liposome tested. No IgG response was detected for the mice immunized with DNP/HA$_2$ in aqueous solution.

Example 7

Effect of a third injection of DNP-CapPE liposomes on the antibody response of mice previously immunized with DNP/HA2 liposomes.

In order to assay the appearance of a memory response towards the DNP target antigen when mice were previously immunized with DNP-CapPE/HA$_2$ liposomes, a group of

TABLE 2

| Liposome Composition | | IgG | Respondent | IgM | Respondent |
|---|---|---|---|---|---|
| DNP-CapPE | HA$_2$ | Titer | Ratio | Titer | Ratio |
| 10 ug | 1 ug | 333 ± 143 | 6/6 | 344 ± 134 | 5/6 |
| 10 ug | 3 ug | 391 ± 124 | 6/6 | 300 ± 165 | 6/6 |
| 10 ug | 9 ug | 766 ± 298 | 6/6 | 336 ± 117 | 6/6 |
| 30 ug | 1 ug | 358 ± 165 | 6/6 | 364 ± 145 | 5/6 |
| 30 ug | 3 ug | 1241 ± 336 | 6/6 | 396 ± 119 | 6/6 |
| 30 ug | 9 ug | 2100 ± 1127 | 6/6 | 1038 ± 445 | 6/6 |
| 10 ug DNP-BSA | | 2245 ± 898 | 6/6 | 0 | 0/6 |
| 10 ug DNP-CapPE and HA$_2$ in aqueous 10 ug* | | 0 | 0/6 | 155 ± 63 | 2/6 |
| + 1 ug* | | 0 | 0/6 | ** | |
| 3 ug* | | 0 | 0/6 | ** | |
| 9 ug* | | 0 | 0/6 | ** | |

*DNP-CapPE and HA$_2$ were incorporated into separate liposomes and administered together.
**Experiment not done.

Example 6

Dose responses to liposomal DNP and HA.2.

In this experiment, three immunization groups were studied. For a given amount of DNP-CapPE (5, 10, 30 ug per injection) varying amount of HA$_2$ (1, 3 or 9 ug) were also incorporated into the liposome preparations composed of EYPC (750 ug/injection). Animals were bled one day before and nine days after an identical booster injection. Sera were analyzed for anti DNP IgG and IgM by ELISA assay. In addition, two groups of mice were immunized with either 10 ug of DNP-BSA, or DNP-CapPE and HA$_2$ mixed together in an aqueous solution.

When IgM ELISA values (Table 2) were analyzed statistically, the two groups representing 5 and 10 ug DNP-CapPE did not show significant differences with increasing amount of HA$_2$ and, therefore, the results of the 5 ug DNP-CapPE group are not shown. However, a significant difference was observed when mice were immunized with liposomes containing 30 ug DNP-CapPE and 1, 3 or 9 ug HA$_2$, the higher ratio giving the higher IgM titer. No IgM response was observed when mice were immunized with 10 ug DNP-BSA, and only 2 out of 6 mice gave a IgM response in the group immunized with DNP-CapPE and HA$_2$ in aqueous solution.

seven mice was injected a third time with liposomes containing only DNP-CapPE (thus providing only the B cell sites). This experiment shows that a memory response is only produced when DNP-CapPE and HA$_2$ are present together in the initial liposome preparation. It also exhibits that the present invention produces a bona fide thymus dependent immunological response and an immunological memory for the target antigen which can produce IgG antibodies in response to the target antigen without a further need for the presence of a T-cell recognition site.

As shown before, mice immunized with DNP-CapPE/HA$_2$ liposomes generated an IgG anti DNP response. When the same mice were then injected a third time with liposomes containing only DNP-CapPE (group 1), SPIRA readings were drastically increased as compared to the first or second bleedings, showing a restimulation of the specific B cells at a higher level than produced by the first immunization. Mice immunized with HA$_2$ liposomes and then restimulated with DNP-CapPE liposomes (group 3) did not produce any detectable anti DNP IgG antibody titer. Mice injected with DNP-CapPE/HA$_2$ liposomes once (group 2) gave the level of anti DNP IgG antibodies for a primary immunization. A control group (group 4) injected with empty EYPC liposomes showed no anti DNP IgG antibody production.

TABLE 3

| Group # | Bleed # | Titer | Respondent Ratio |
|---|---|---|---|
| 1 | 1 | 1974 ± 975 | 7/7 |
|   | 2 | 817 ± 270 | 7/7 |
|   | 3 | 4071 ± 1058 | 7/7 |
| 2 | 1 | 158 ± 28 | 3/7 |
|   | 3 | 288 ± 75 | 3/7 |
| 3 |   | 0 | — | 0 |
| 4 |   | 0 | — | 0 |

Example 8

Outer membrane HA2 versus internal HA2 in the immune response.

Four groups of outbred mice were immunized with EYPC liposomes composed of 30 ug of DNP-CapPE and various amounts of HA (3, 1, 0.5 and 0 ug). In addition, a group of mice was immunized with DNP-CapPE/HA$_2$ liposomes (30 and 3 ug respectively) after previous treatment of the liposomes with bromelain (100 ug/ml). Treatment with bromelain cleaves surface proteins, leaving only the membrane inserted tail and intact internalized HA$_2$. When ELISA titer were analyzed statistically, a dose response effect was observed again with increasing amount of HA$_2$. Table 4. As little as 0.5 ug of HA$_2$ in DNP-CapPE liposomes per injection, was sufficient to induce an IgG response statistically different from DNP-CapPE liposomes. No statistical difference, however, was observed when mice were immunized with bromelain treated liposomes as compared to the response obtained for the same untreated liposomes. These results indicate that the HA$_2$ outside the liposomes was not required, and that liposomes must be processed in order to realize the combined presentation of B and T cell epitopes to the immunocompetent cells.

TABLE 4

| Group # | Liposome Composition DNP-CapPE | HA$_2$ | IgG Titer | Respondent Ratio |
|---|---|---|---|---|
| 1 | 30 ug | 3 ug | 944 ± 291 | 7/7 |
| 2 | 30 ug | 1 ug | 471 ± 97 | 7/7 |
| 3 | 30 ug | 0.5 ug | 438 ± 121 | 7/7 |
| 4 | 30 ug | 0 | 198 ± 88 | 2/7 |
| 5 | group 1 after bromelain treatment of liposomes |  | 808 ± 315 | 7/7 |

Example 9

IgG Immunoglobulin subclasses repartition during the immune response.

When ELISA readings were analyzed, IgG1 antibody was the predominant subclass.

The IgG1 response of outbred mice to DNP was similar for low doses of DNP-CapPE (Table 1) at different HA$_2$ concentrations. For higher concentration of DNP-CapPE (30 ug), a dose response effect was observed for increasing amounts of HA$_2$. A liposome preparation of EYPC, DNP-CapPE and HA$_2$ of 750, 30 and 9 ug respectively, gave an IgG1 response comparable to the group of mice immunized with 10 ug of DNP-BSA, a typical hapten carrier system.

No significant differences were observed with the IgG2a and IgG2b antibodies subclasses (Table 5). The only group for which no IgG2a or IgG2b antibodies could be detected were the groups of mice immunized with EYPC liposomes containing 1 ug HA$_2$ and 10 ug DNP-CapPE (IgG2a and IgG2b) and 3 ug HA$_2$ and 10 ug DNP-CapPE (IgG2b). For higher dose of DNP-CapPE or HA$_2$, no significant differences in the responses were observed. The responses were comparable to those when mice were immunized with DNP-BSA.

No significant difference was observed with the IgG3 antibody subclass. For each group, titer were detected and at least 4 of the 6 mice immunized responded (Table 5). However, only 2 mice immunized with 10 ug DNP-BSA responded, raising titer significantly lower than the groups of mice immunized with the liposome preparations.

TABLE 5

| Liposome Composition DNP-CapPE | HA$_2$ | Respondent Ratio | Titer | Respondent Ratio | Titer |
|---|---|---|---|---|---|
|  |  | IgG$_1$ |  | IgG$_{2a}$ |  |
| 10 ug | 1 ug | 3/6 | 180 ± 70 | 0/6 |  |
| 10 ug | 3 ug | 4/6 | 222 ± 79 | 4/6 | 190 ± 50 |
| 10 ug | 9 ug | 6/6 | 255 ± 52 | 6/6 | 241 ± 78 |
| 30 ug | 1 ug | 4/6 | 275 ± 102 | 4/6 | 326 ± 92 |
| 30 ug | 3 ug | 6/6 | 370 ± 186 | 6/6 | 366 ± 126 |
| 30 ug | 9 ug | 6/6 | 803 ± 402 | 6/6 | 371 ± 77 |
| 10 ug DNP-BSA |  | 6/6 | 941 ± 578 | 6/6 | 258 ± 85 |
| 10 ug DNP-CapPE 3 ug HA$_2$, aqueous |  | 0/6 |  | 0/6 |  |
|  |  | IgG$_{2b}$ |  | IgG$_3$ |  |
| 10 ug | 1 ug | 0/6 | 180 ± 70 | 4/6 | 177 ± 20 |
| 10 ug | 3 ug | 0/6 |  | 4/6 | 217 ± 93 |
| 10 ug | 9 ug | 5/6 | 308 ± 21 | 5/6 | 280 ± 96 |
| 30 ug | 1 ug | 2/6 | 223 ± 104 | 5/6 | 280 ± 105 |
| 30 ug | 3 ug | 5/6 | 250 ± 141 | 6/6 | 333 ± 110 |
| 30 ug | 9 ug | 6/6 | 275 ± 91 | 6/6 | 376 ± 71 |
| 10 ug DNP-BSA |  | 5/6 | 302 ± 98 | 2/6 | 190 ± 28 |
| 10 ug DNP-CapPE 3 ug HA$_2$, aqueous |  | 0/6 |  | 0/6 |  |

The invention now being fully described, it will be apparent to one of ordinary skill in the art that changes and modifications can be made thereto without departing from the spirit or scope of the invention as set forth herein.

I claim:

1. A liposomal immunogenic carrier for antigens, consisting essentially of a liposome-forming lipid, a 'N-2(2,4 dinitrophenyl E-aminocaproylphosphatidylethanolamine' target antigen and at least one helper peptide having at least one T-helper cell recognition site, wherein said T-helper cell recognition site is in or on the liposome and wherein said target antigen and helper peptide are not bound to each other, and wherein said helper peptide is HA$_2$ polypeptide subunit of influenza virus.

2. A liposomal immunogenic carrier according to claim 1 comprising a lipid selected from the group consisting of a phosphatidyl ether, phosphatidyl ester, cerebroside, ganglioside, sphingomyelin, and mixtures thereof.

3. A liposomal immunogenic carrier according to claim 1, wherein said helper peptide is associated inside the liposome via hydrophobic interactions.

4. A liposomal immunogenic carrier according to claim 1, wherein the helper peptide is associated inside the liposome by a covalent link to a liposome-forming lipid.

5. A liposomal immunogenic carrier according to claim 1, wherein the carrier comprises approximately one $HA_2$ molecule per 120,000 lipid molecules.

6. A method for eliciting an immune response in mammals against a target antigen comprising administering to an animal an immunogenic amount of a liposomal immunogenic carrier of claim 1.

7. A method for eliciting an immune response in mammals against a target antigen comprising administering to an animal an immunogenic amount of a liposomal immunogenic carrier of claim 2.

8. A method for eliciting an immune response mammals against a target antigen comprising administering to an animal an immunogenic amount of a liposomal immunogenic carrier of claim 3.

9. A method for eliciting an immune response in mammals against a target antigen comprising administering to an animal an immunogenic amount of a liposomal immunogenic carrier of claim 4.

10. A method for eliciting an immune response mammals against a target antigen comprising administering to an animal an immunogenic amount of a liposomal immunogenic carrier of claim 5.

11. A liposomal immunogenic carrier according to claim 2, wherein phosphatidyl esters are selected from the group consisting of phosphatidylethanolamine and phosphatidylcholine 12. A liposomal immunogenic carrier according to claim 2, wherein said steroid is cholesterol.

* * * * *

UNITED STATES PATENT AND TRADEMARK OFFICE
CERTIFICATE OF CORRECTION

PATENT NO. : 5,464,630

DATED : November 7, 1995

INVENTOR(S) : Howard R. Six and Nathalie B. Garcon

It is certified that error appears in the above-indentified patent and that said Letters Patent is hereby corrected as shown below:

Column 2, line 58, "cahains" should read -- chains --.

Column 4, line 23, "Similary," should read -- Similarly, --

Column 5, line 26, "was used To" should read -- was used. To --.

Column 7, line 10, (first column in TABLE 1), "DNA-" should read -- DNP- --.

Column 7, (TABLE 2--the last three rows of the first column heading "DNP-CapPE") reading:

$$+ 1 \text{ ug}^*$$
$$3 \text{ ug}^*$$
$$9 \text{ ug}^*$$

should be moved and re-inserted as the last three rows of the second column heading "$HA_2$".

Column 7, line 45, "HA 2" in the heading under Example 6 should read -- $HA_2$ --.

Column 8, line 9, "does" should read -- dose --.

UNITED STATES PATENT AND TRADEMARK OFFICE
CERTIFICATE OF CORRECTION

PATENT NO. : 5,464,630

DATED : November 7, 1995

INVENTOR(S) : Howard R. Six and Nathalie B. Garcon

It is certified that error appears in the above-indentified patent and that said Letters Patent is hereby corrected as shown below:

Column 11, line 14, (first line of Claim 8) "immune response mammals" should read -- immune response in mammals --.

Signed and Sealed this

Eighth Day of July, 1997

*Attest:*

BRUCE LEHMAN

*Attesting Officer*     *Commissioner of Patents and Trademarks*